United States Patent [19]

Hwang

[11] Patent Number: 4,795,428

[45] Date of Patent: Jan. 3, 1989

[54] THERAPEUTIC SUCTION DEVICE

[76] Inventor: Shyh-Chyi Hwang, No. 427-9, Fu-Hsing Rd., Fu-Hsing Tsun, Yung-Kang Hsiang, Tainan Hsien, Taiwan

[21] Appl. No.: 32,363

[22] Filed: Mar. 30, 1987

[51] Int. Cl.$^4$ .............................................. A61M 1/06
[52] U.S. Cl. ....................................... 604/73; 604/315; 604/319; 604/320; 604/902; 604/118; 604/119
[58] Field of Search ............... 604/19, 35, 73, 313, 604/315, 319, 320, 902, 118, 119; 417/279, 285, 297, 28, 317, 295

[56] References Cited

U.S. PATENT DOCUMENTS

| 2,651,263 | 9/1953 | Mathews | 417/28 |
| 2,655,306 | 10/1953 | Neff | 417/28 |
| 3,086,528 | 4/1963 | Eichelman et al. | 604/49 |
| 3,446,238 | 5/1969 | Norstrnd et al. | 417/28 |
| 3,558,239 | 1/1971 | Schiber | 417/28 |
| 3,599,639 | 8/1971 | Spotz | 604/119 |
| 4,065,230 | 12/1977 | Gezari | 417/317 |
| 4,180,074 | 12/1979 | Murry et al. | 604/119 |
| 4,315,506 | 2/1982 | Kayser et al. | 604/73 |
| 4,369,785 | 1/1983 | Rehkopf et al. | 604/123 |
| 4,396,386 | 8/1983 | Kurtz et al. | 604/319 |
| 4,545,740 | 10/1985 | Nishikiori et al. | 417/317 |
| 4,560,323 | 12/1985 | Orchard | 417/28 |
| 4,670,006 | 6/1987 | Sinnett et al. | 604/119 |
| 4,706,687 | 11/1987 | Rogers | 604/119 |
| 4,718,895 | 1/1988 | Kurtz et al. | 604/319 |

Primary Examiner—John D. Yasko
Assistant Examiner—Gene B. Kartchner
Attorney, Agent, or Firm—McCormick, Paulding & Huber

[57] ABSTRACT

A therapeutic suction device includes an operating vacuum chamber connected to a motor operated pump to create a vacuum pressure therein and a pressure controlling means to maintain a predetermined pressure in the vacuum chamber. The vacuum pressure in the operating vacuum chamber can be pre-arranged so as to provide a suction force by a pressure difference even when there is a shortage of electricity.

7 Claims, 3 Drawing Sheets

THERAPEUTIC SUCTION DEVICE

BACKGROUND OF THE INVENTION

The present invention relates to a therapeutic suction device and particularly to one with a vacuum pressure controlling means to control the suction pressure of the device and an operating vacuum chamber kept at a controlled vacuum pressure to effect a suction by a pressure difference.

There are different therapeutic suction devices, such as those for suctioning phlegm, a liquid from the stomach or the thorax of a patient body, etc. These suction devices typically include an electrically operated pump to effect suction, and are designed differently to operate at different suction pressures according to the kind of liquid to be suctioned from a patient body. For instance, to suction the liquid from the stomach the suction pressure must be maintained from 100-120 mmHg, and to suction viscous liquid the suction pressure must be maintained from 300-400 mmHg. A suction device with a suitable suction pressure must be carefully chosen because if the pressure is too high it may harm the patient and if the pressure is too low it may render the suction ineffective. Furthermore, if there is a shortage of electricity during the suction operation, the operation can not continue and the suction device must be turned off so that the communication between the pump and the patient body is halted immediately. Therefore, the conventional devices are inconvenient.

SUMMARY OF THE INVENTION

An object of the invention is to provide a therapeutic suction device that can effect a suction of a liquid from a patient body with a predetermined suction pressure.

Another object of the invention is to provide a therapeutic suction device including an operating vacuum chamber by which the device can operate even when there is a shortage of electricity.

According to the present invention, a suction device comprises a vacuum chamber, means for creating a vacuum pressure in the chamber, including a pump connected to the vacuum chamber, a solenoid valve for interrupting the communication between the pump and the vacuum chamber, an electric power means for operating the vacuum pressure creating means, a control circuit means to control the power means, a first pressure controlling means for detecting the pressure in the vacuum chamber and for deenergizing the control circuit in response to a predetermined suction pressure of the vacuum chamber, a container means for receiving a liquid suctioned from a patient body, communicated with the vacuum chamber and having a liquid inlet means, and a valve means for opening and closing the liquid inlet means.

In one aspect of the invention, the control circuit means includes a normally closed microswitch to be actuated by the pressure controlling means, and a relay in circuit with said microswitch, said motor and said solenoid valve means.

In another aspect of the invention, the pressure controlling means includes a main pressure controlling bellow to be maintained at a first predetermined suction pressure therein, communicated with the vacuum chamber, the bellow having a fixed end and a movable end, means for actuating the microswitch of the control circuit when the first predetermined suction pressure is reached, having a stem with one end thereof connected to the movable end of the bellow, and an adjustment means to set the pressure of the bellow at the predetermined pressure.

In further aspect of the invention, the container means includes a plurality of container units and the pressure controlling means further includes a plurality of sup-pressure controlling bellows each communicated with the main pressure controlling bellow to be maintained at a second predetermined suction pressure lower than the first predetermined pressure, and communicated with each of the container units.

In still further aspect of the invention, the liquid inlet valve means includes a valve casing, having a rear end, a forward end and a passage extending from the rear end to the forward end, and an operating means having a valve plug means normally closing the passage and a push button to push the plug means to a position opening the passage.

The present exemplary preferred embodiment will be described in detail with reference to the following drawings, in which:

DETAILED DESCRIPTION OF THE PREFERRED EMBODIMENT

Figure 1:
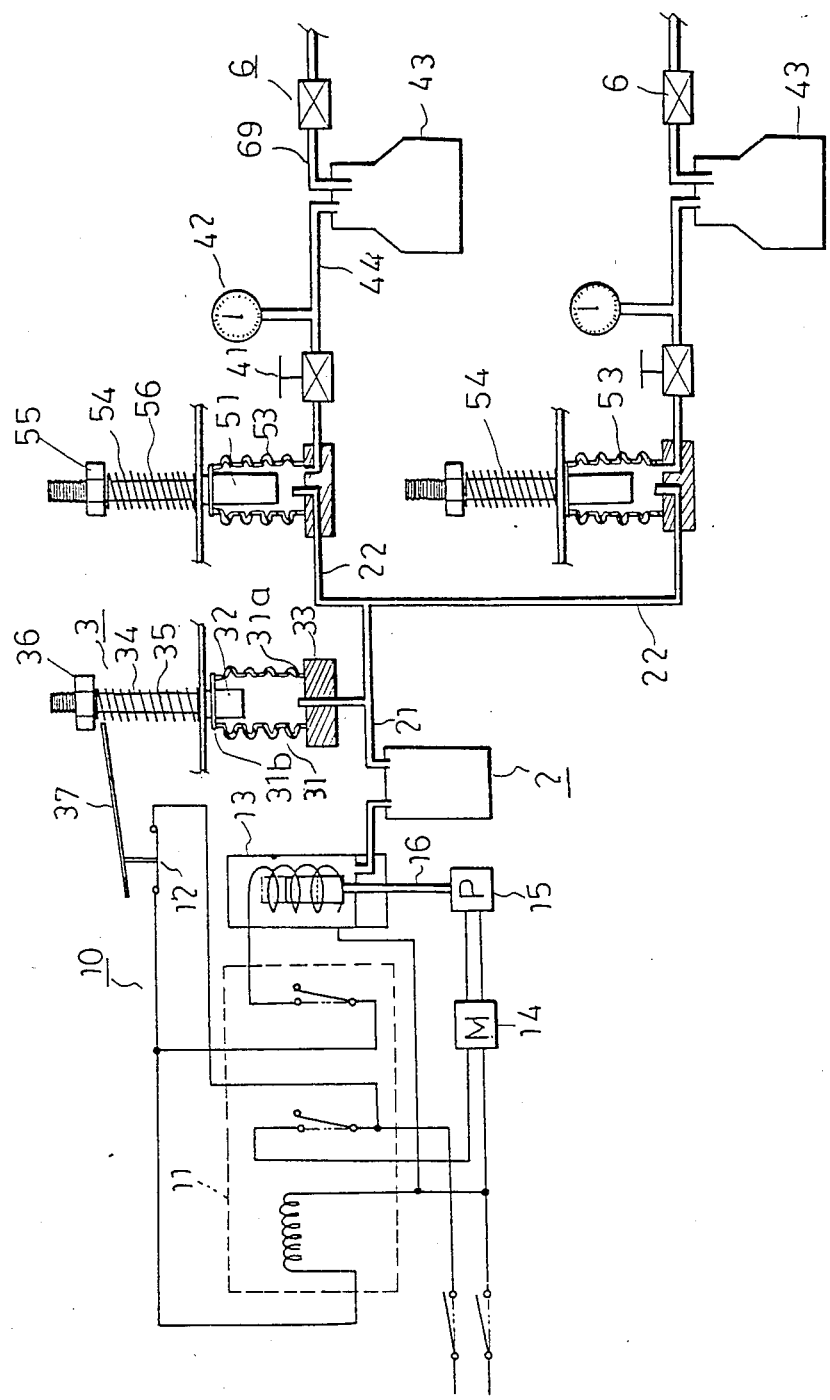
FIG. 1 is a schematic view showing an embodiment of a suction device according to the present invention.
Figure 2:
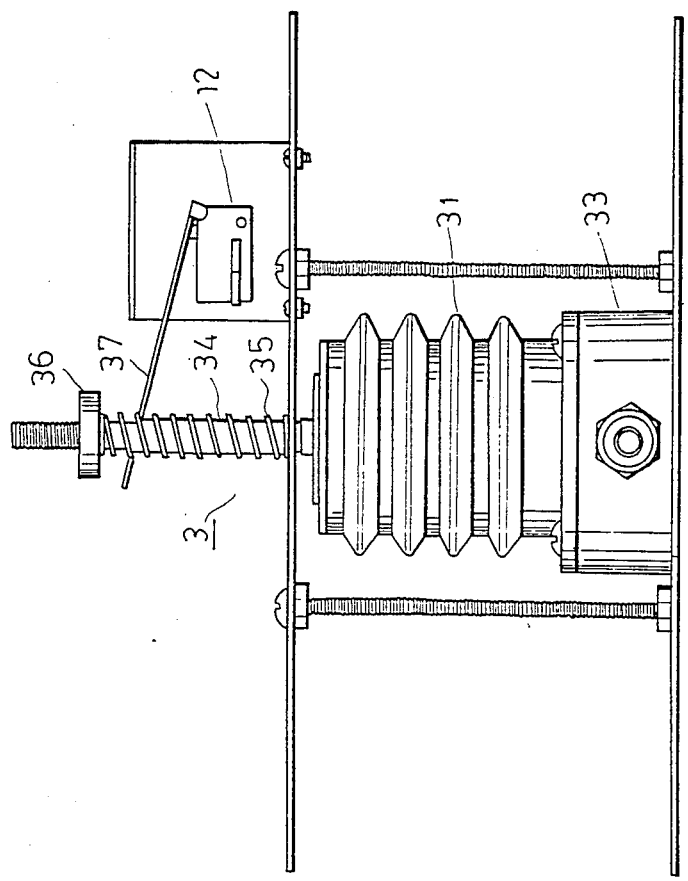
FIG. 2 is a schematic view of a pressure controlling means of the suction device.
Figure 3:
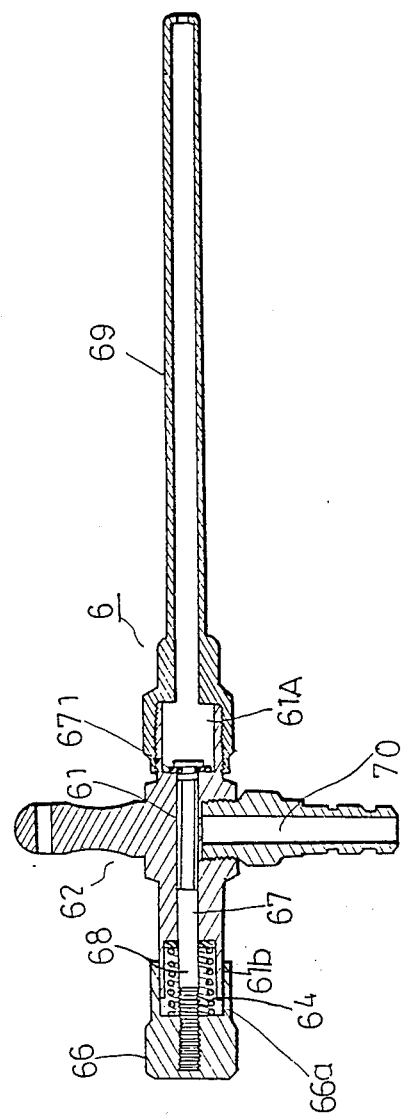
FIG. 3 is a schematic view of an inlet valve means of the suction device.

Referring to the drawings, there is shown a therapeutic suction device which includes a vacuum chamber 2, a motor 14 and a pump 15 for creating a vacuum pressure in the chamber 2, and a control circuit 10 in connection with a power source (not shown) for controlling the motor 14. The control circuit 10 includes a normally closed microswitch 12 for opening the circuit 10 when the vacuum pressure in the chamber 2 reaches a predetermined pressure, a relay 11 in circuit with the microswitch 12, the motor 14 and a solenoid valve 13. The pump 15 is communicated with the chamber 2 through a conduit 16 and the solenoid valve 13 is disposed at a location of the conduit 16 for interrupting the communication between the pump 15 and the chamber 2. When the control circuit 10 is closed, the motor 14 operates the pump 15, creating a vacuum pressure in the chamber 2. When the microswitch 12 is opened to deenergize the circuit 10 by means of a pressure controlling means 3, the operation of the motor 14 and pump 15 stops and the solenoid valve 13 interrupts the communication between the pump 15 and the chamber 2.

During the operation of the suction device, the pressure controlling means 3 controls the microswitch 12 as well as the circuit 10 so as to maintain a predetermined vacuum pressure in the chamber 2. The vacuum pressure in the chamber 2 can be maintained even when there is a shortage of electricity by the interruption of the solenoid valve 13.

The pressure controlling means 3 is connected to the chamber 2, and includes a main pressure controlling bellow 31 which has a fixed end 31a mounted on a support 33 and is connected to the conduit 21 through a manifold so as to be communicated with the bellow 31. The bellow 31 further has a movable end 31b to which a stem 34 is connected. The stem 34 is axially movable and has one end portion 32 extending into the bellow 31 and the other end portion which is threaded and to which is attached an adjustment nut 36. A spring 35 is sleeved around the stem 34 to bias the movable end 31b toward to the fixed end 31a so as to set the movable end at a certain distance from the fixed end by adjusting the nut 36. When a vacuum pressure is created in the bellow 31 and in the vacuum chamber 2, the movable end 31b moves toward the fixed end and the nut 36 moves towards the microswitch 12. When the nut 36 actuates a lever 37 of the microswitch 12, the microswitch 12 is turned off. In this situation, the motor is stopped and the solenoid valve 13 is closed, interrupting the communication between the chamber 2 and the pump 15. A predetermined pressure is thereby maintained in the vacuum pressure chamber 2. The vacuum pressure in the chamber 2 is adjusted by the adjustment of the nut 36. When the suction or vacuum pressure decreases due to the application of the suction device, the stem 34 will move away from the fixed end 31a and the nut 36 will move away from the lever 37 of the microswitch 12. Accordingly, the circuit 10 will be closed again and the pump will operate again.

In order to connect the vacuum chamber 2 to two liquid flasks or more than two liquid flasks, the conduit 21 of the vacuum chamber 2 can be arranged with a manifold arrangement. As is shown in the drawings, the pressure controlling means 3 further includes two sup-pressure controlling bellows 53 which are connected to the conduit 21 through manifolds 22. Each bellow 53 has a fixed end through which each manifold 22 extends into the bellow 53, and has the other end movable and connected to a movable stem 54. Each stem 54 has a head portion 51 extendng into the bellow 53 through the movable end 52. Opposite the head portion 51 is an adjustment nut 55 and a spring 56. By adjusting the nut 55, the pressure in the bellow 53 can be adjusted. When the vacuum pressure in the bellow 53 reaches a predetermined value, the movable end of the bellow 53 moves toward the fixed end, and the head portion 51 blocks up the opening of the manifold 22, interrupting the communication between the bellow 53 and the vacuum chamber 2. The vacuum pressure maintained in each bellow 53 is lower than that in the bellow 31.

Each bellow 53 is connected to a liquid flask 43 through a conduit 44. The liquid flask 43 is provided with an inlet conduit 69 which will be directed into a patient body. Between the liquid flask 43 and the bellow 53 is provided a pressure gauge 42 and a valve 41. An inlet valve means 6 is disposed at the inlet conduit 69 of each liquid flask 43.

Each valve means 6 includes a valve casing 62 which has a passage 61 extending from a forward end 61a and a rear end 61b of the casing 62. An operating rod 67 is inserted movably in the passage 61 and an operating knob 66 which is connected integrally with the operating rod 67 has a sleeve portion 66a sleeved slideably around the rear end 61b of the valve casing 62. A spring 64 is received in the rear end 61b and sleeved around the rear portion 68 of the operating rod 67. A conduit 70 is screwed to the valve casing 62 to communicate with the passage 61 and is directed to the liquid flask 43. The forward end 61a of the valve casing is connected to the conduit 69. At a front end of the operating rod 67 is a valve plug 671 which normally blocks up the front end of the passage so that the conduits 69 and the conduit 70 are not intercommunicated. When in use, one may just push the operating knob 66 forward to effect the suction operation.

When the liquid flask 43 is full, it can be replaced by a next flask by closing the valve 41 and detaching the liquid filled flask 43 from the suction device.

While the above-described embodiment includes a main pressure controlling bellow 31 and two sup-pressure controlling bellows 53, the invention is not limited thereto. The suction device of the invention may include a single pressure controlling bellow or a main pressure controlling bellow with more than two sup-pressure controlling bellows. It can be appreciated that the vacuum pressure created in the chamber 2 provides a suction force even when there is a shortage of electricity.

With the invention thus explained, it is apparent that various modifications and variations can be made without departing from the scope of the invention. It is therefore intended that the invention be limited as indicated in the appended claims.

What I claim is:

1. A therapeutic suction device for suctioning a patient's body cavity and comprising:
    means defining a vacuum chamber,
    a vacuum pressure source, a solenoid valve between said vacuum chamber and said source,
    electrically controlled means for said vacuum pressure source and including a control circuit, means for detecting the pressure in said vacuum chamber,
    limit switch means in said control circuit and responsive to said vacuum pressure detecting means,
    tube means for insertion into a patient's body cavity and including inlet valve means,
    container means for receiving liquid suctioned by said tube means,
    a chamber of variable volume communicating with said vacuum chamber, said variable volume chamber having a fixed end and a movable end, said detecting means including means for operating said limit switch as a result of movement by said movable end of said variable volume chamber.

2. The suction device according to claim 1 wherein said means for moving said limit switch includes adjustment means to vary the vacuum pressure required to move said limit switch.

3. The suction device according to claim 2 wherein said adjustment means includes a threaded stem, an adjustment nut on the stem, and a spring acting between said adjustment nut and the movable end of said variable volume chamber.

4. The suction device according to claim 2 wherein said container means comprises a plurality of individual fluid container units.

5. The suction device according to claim 4 further characterized by individual variable volume chambers associated with each of said fluid container means, each of which variable volume chambers is in communication with said vacuum chamber, and individual valve means between each of said variable volume chambers associated with said individual container units.

6. The suction device according to claim 5 wherein each individual variable volume chamber associated with the individual container unit includes a movable and a fixed end, and means supporting said movable end including a spring, and adjustment means to vary the individual suction pressure associated with each individual container unit and associated variable volume chamber, said individual suction pressure being adjusted to be lower then the pressure detected by said limit switch.

7. The suction device according to claim 1 wherein said inlet valve means comprises a valve casing having a rear end, a forward end, and a passage extending from the rear to the forward end, and an operating rod having a forward end with a valve plug normally biased to close said passage, said operating rod having a rear end defining a push button for pushing said plug to a position opening said passage.

* * * * *